US005143940A

United States Patent [19]

Nurnberg et al.

[11] Patent Number: 5,143,940

[45] Date of Patent: Sep. 1, 1992

[54] AMBIPHILE CREAM

[75] Inventors: Eberhard Nurnberg, Uttenreuth/Weiher; Uwe Leonhardt, Topen; Otto P. Hornstein, Uttenreuth; Gabriele Griessmeyer, Erlangen; Harald Perschbacher, Bad Homburg von der Hohe, all of Fed. Rep. of Germany

[73] Assignee: Stada Arzneimittel AG, Bad Vilbel, Fed. Rep. of Germany

[21] Appl. No.: 630,729

[22] Filed: Dec. 20, 1990

Related U.S. Application Data

[63] Continuation of Ser. No. 333,388, Mar. 31, 1989, abandoned.

[30] Foreign Application Priority Data

Apr. 8, 1988 [EP] European Pat. Off. ........... 88105632

[51] Int. Cl.[5] ............................................. A61K 47/00

[52] U.S. Cl. .................................... 514/785; 514/786; 514/941; 514/943

[58] Field of Search ................ 514/785, 786, 941, 943

[56] References Cited

U.S. PATENT DOCUMENTS 4,246,285 1/1981 Van Duzee ..................... 514/938 X 4,424,234 1/1984 Alderson et al. .................. 424/317

FOREIGN PATENT DOCUMENTS 0226337 6/1987 European Pat. Off. .

OTHER PUBLICATIONS

M. Cajkovac et al., "Influence of Vehicle on Antimicrobial Efficiency of Topical Dosage Forms of Chloramphenicol", Pharmazie, vol. 42, Nov. 5, 1987, pp. 327–329.

S. Bartkowicz et al., "Changes in the Pharmaceutical and Biological Availability of Aminophylline from Suppositories in the Presence of Nonionic Surfactants in the Course of One Year Storage", Chemical Abstracts, vol. 104, 1986, p. 425.

*Primary Examiner*—Leonard Schenkman

*Attorney, Agent, or Firm*—Wegner, Cantor, Mueller & Player

[57] ABSTRACT

Ambiphilic creams with improved spreading and penetration properties as well as improved tolerance contain a glycerol-monostearate-free water-in-oil emulsifier and glycerol and/or sorbitol. Ambiphilic creams with an isopropyl myristate content have particularly favorable properties.

17 Claims, No Drawings

AMBIPHILE CREAM

This application is a continuation of United States application Ser. No. 07/333,388 filed Mar. 31, 1989, abandoned.

Ambiphilic creams are known as spreadable emulsions that contain a fatty phase, a water phase and both a water-in-oil and an oil-in-water emulsifier as the main constituents. They are characterized by an extremely fine phase dispersion. Thus, the ambiphilic nature can be recognized most simply by the fact that a droplet-like dispersion of the fatty phase in the water phase is no longer clearly perceptible in microscopic examinations. Under the polarizing microscope they give the impression of a bicoherent phase system, i.e., that the fatty phase and the water phase coexist, neither of the two phases being included by the other. Although ambiphilic creams are formally classified as hydrophilic cream systems, they are dilutable or miscible with lipid-like substances, such as, for example, hydrocarbons, vegetable or synthetic oils and the like, just as they are also always miscible with water.

The quantitative proportions of the lipids or lipid-like substances forming the fatty phase generally lie in such a range that the ambiphilic creams can be regarded as a kind of excessively fatty oil-in-water cream.

As a further constituent, the ambiphilic creams heretofore known have contained propylene glycol (1,2-propanediol) as an emollient and humectant. Besides this, propylene glycol also has antimicrobial properties.

Ambiphilic creams are the subject matter of intensive studies (E. Nürnberg, Arzneimittelforschung 1966, 14; Arzneimittelforschung 1968, 11; and Deutsche Apothekerzeitung, 1968, 907; R. Muckenschnabel, "Hydrophilic and ambiphilic cream systems—Contribution to the knowledge of the structure and galenic properties", Dissertation, Erlangen 1986):

| Muckenschnabel | |
|---|---|
| Glycerol monostearate | 4.0 g |
| Polyoxyethylene glycerol monostearate | 7.0 g |
| Medium-chain-length triglycerides | 7.5 g |
| Cetyl stearyl alcohol | 6.0 g |
| Propylene glycol | 10.0 g |
| White vaseline | 25.5 g |
| Water | 40.0 g |

To prevent undesired crystal growth of the active pharmaceuticals contained in the creams, the said creams can contain colloids, especially hydrocolloids, such as gelatin or collagen or methyl- and hydroxypropylmethycellulose.

An ambiphilic cream by the name of Cremor basalis is also known from the DAC, i.e., the German Drug Codex.

| Cremor basalis | |
|---|---|
| Glycerol monostearate | 4.0 g |
| Cetyl alcohol | 6.0 g |
| Medium-chain-length triglycerides | 7.5 g |
| White vaseline | 25.5 g |
| Polyoxyethylene glycerol monostearate | 7.0 g |
| Propylene glycol | 10.0 g |
| Water | 40.0 g |

The special advantage of the ambiphilic cream bases lies in their capability to release water-soluble and fat-soluble active pharmaceuticals without hindrance. Nevertheless, it has been shown that the known ambiphilic creams need to be further improved in terms of their consistency and their spreading and penetration qualities, in addition to tolerance problems that have been observed for some time.

Instead of stabilizers such as p-hydroxybenzoic acid that frequently cause contact allergies, known ambiphilic creams contain, as the antimicrobial substance, propylene glycol, that at the same time acts as an emollient and humectant. However, these galenic advantages are countered by therapeutic dermatological disadvantages, since even propylene glycol has sensitizing and irritating effects. The attempt to replace this polyhydric alcohol by glycerol or sorbitol has, however, led to a loss of the ambiphilic character that could not have been predicted.

Unexpectedly, it has now been found that ambiphilic creams that are independent or free of propylene glycol can nevertheless be prepared with a content of glycerol or sorbitol under specified conditions that were not foreseeable by one skilled in the art. A prerequisite for the use of glycerol or sorbitol is to dispense with glycerol monostearate as a component of the water-in-oil emulsifier mixture, in other words, for example, to use only one water-in-oil emulsifier such as, for example, an aliphatic alcohol (fatty alcohol). This fact was unexpected because it is precisely the mixture of, for example, glycerol monostearate and fatty alcohols that has been regarded as particularly favorable for the formulation of ambiphilic creams (see above-mentioned formulations and literature). A further possibility for the preparation of ambiphilic creams that replace propylene glycol involves an additional content of isopropyl myristate. In fact, compared with the use of glycerol or sorbitol alone, this simultaneously represents are alternative approach. Isopropyl myristate can be incorporated in particular as a component of the lipid phase. In the presence of isopropyl myristate, with or without glycerol or sorbitol, the restrictions in the water-in-oil emulsifier cease to apply, i.e., a water-in-oil emulsifier mixture, e.g., of the above-mentioned type, can once again be employed without problems. It has been shown unexpectedly that a content of isopropyl myristate is quite generally accessible for application in ambiphilic creams. Such a content not only makes it possible to improve the ambiphilic character regardless of type and quantity of the emulsifiers, of any propylene glycol contents that may be present and of other constituents, but it also provides an excellent spreadability and improved tolerance.

An important feature of the novel ambiphilic creams of this invention is the content of a complex emulsifier system. By this term there are understood mixtures of an oil-in-water and a water-in-oil emulsifier, a weak water-in-oil emulsifier frequently being added in appropriately higher proportion. Polyoxyalkylated esters, preferably polyoxyethylene glycerol monostearate containing about 18 to about 20 oxyethylene groups and having HLB values in the range of 15 are used as the hydrophilic oil-in-water emulsifier. Higher fatty alcohols, fatty alcohol mixtures, partial esters of glycerol and the like are used in particular as water-in-oil emulsifiers. Cetyl stearyl alcohols in which cetyl alcohol and stearyl alcohol are present in a mixing ratio of approximately 1:1 have proved effective as fatty alcohol mixtures. Mixtures of oil-in-water emulsifiers and/or mixtures of water-in-oil emulsifiers can also be used. Thus, the use of cetyl stearyl alcohols together with glycerol monostearate is advantageous, the stability being markedly promoted by the glycerol monostearate. For this purpose it is also possible to use commercial glycerol monostearate products that also contain di- and triglycerides as well as small amounts of free glycerol and free fatty acids. Such commercial products are preferred. Usually nonionic compounds are used as oil-in-water and water-in-oil emulsifiers. The weight ratios of oil-in-water emulsifier to water-in-oil emulsifier are generally between 1:1 and 1:2, especially in the range of 1:1.5.

The ambiphilic creams according to the invention can contain glycerol and/or sorbitol, preferably in proportions of 1 to 20 weight percent, especially 5 to 15 weight percent, most preferably 10 weight percent. In this connection the presence of paraffin hydrocarbons has proved particularly effective.

Isopropyl myristate, which is a liquid lipid, can be incorporated, for example, as the sole fatty phase, which leads to particularly soft creams. In such cases the content of isopropyl myristate is between 20 and 50 weight percent, preferably between 25 and 35 weight percent, especially 30 weight percent. Besides isopropyl myristate, it is also possible, especially within the above-mentioned quantitative figures that are applicable for the total fatty phase, to use other known constituents of the fatty phase of ambiphilic creams, such as liquid, especially viscous paraffin, vaseline, medium-chain-length triglycerides, mainly of capric and caprylic acid, 2-octyldodecanol, etc., although care must be taken that such use does not detract from the ambiphilic character. The observation of the loss of the ambiphilic character due to replacement of the propylene glycol by glycerol or sorbitol unless the procedure according to the invention is followed, and the preservation of the ambiphilic character by isopropyl myristate independently of propylene glycol, are all the more unexpected. This is because of the view held heretofore by those skilled in the art that the ambiphilic character is exclusively the result of the correct combination of oil-in-water and water-in-oil emulsifiers, and that it does not also depend on the nature of other constituents, e.g., those forming the fatty phase. By the procedure of the invention it is possible to replace propylene glycol completely or to the desired extent or to prepare ambiphilic creams that, if desired, are completely free of propylene glycol.

The subject matter of the invention also comprises ambiphilic creams with a content of water and lipids or lipid-like substances, nonionic oil-in-water and water-in-oil emulsifiers and, as desired, further constituents such as stabilizers, spreading agents, emollients, humectants, crystallization inhibitors and/or active pharmaceuticals and the like. These creams have a water content of 25 to 55 weight percent, especially 38 to 45 weight percent and most preferably 40 to 43 weight percent, a content of 1 to 20 weight percent, preferably 7 to 15, especially 10 weight percent, of glycerol and/or sorbitol, and/or a content of isopropyl myristate of 20 to 50 weight percent, especially 30 weight percent, as desired together with further lipid-like substances, in each case relative to the total weight of the ambiphilic cream.

Frequently a content of crystallization-inhibiting agents has proved advantageous for preventing the crystal growth of the active substances. Examples of such agents are, in particular, colloids, preferably gelatin, or also other hydrocolloids, although other known crystallization inhibitors are not ruled out thereby. Such agents, such as gelatin, can be incorporated in proportions of 0.1 to 5, preferably 0.3 to 1 weight percent.

The invention is further illustrated by reference to the following non-limiting examples of formulations.

| | Ex. 1 | Ex. 2 | Ex. 3 | Ex. 4 | Ex. 5 | Ex. 6 |
|---|---|---|---|---|---|---|
| | Parts by Weight | | | | | |
| Polyoxyethylene glycerol monostearate (Tagat ® S2) | 7.0 | 7.0 | 7.5 | 7.0 | 7.5 | 7.5 |
| Glycerol monostearate (Tegin ® M) | 4.0 | 4.0 | 4.0 | 4.0 | — | — |
| Cetyl stearyl alcohol (Lanette ® O) | 6.0 | 6.0 | 6.0 | 6.0 | 10.0 | 10.0 |
| Viscous paraffin (PS) | 10.0 | 15.0 | 15.0 | — | 30.0 | 25.0 |
| Isopropyl myristate (IPM) | 20.0 | 5.0 | 7.5 | 20.0 | — | — |
| 2-Octyldodecanol (Eutanol ® G) | — | — | 7.5 | 5.0 | — | — |
| Medium-chain-length triglycerides (Miglyol ® 812) | — | 10.0 | — | 5.0 | — | — |
| Glycerol | 10.0 | 10.0 | 10.0 | 10.0 | 10.0 | 10.0 |
| Water | 42.5 | 43.0 | 42.0 | 42.5 | 41.9 | 47.1 |
| Gelatin | 0.5 | — | 0.5 | 0.5 | 0.5 | — |
| Stabilizers | q.s. | q.s. | q.s. | q.s. | q.s. | q.s. |

What is claimed is:

1. An ambiphilic cream base consisting essentially of:

(a) water, and lipids or lipid-like substances forming a fatty phase.

(b) oil-in-water and water-in-oil emulsifiers, and (c) glycerol, sorbitol or mixtures thereof, wherein each of the components is present in an amount effective to provide an ambiphilic cream, and provided that the ambiphilic cream contains no glycerol monostearate or propylene glycol.

2. An ambiphilic cream base according to claim 1, wherein glycerol is present at 1 to 20 percent by weight of the ambiphilic cream base.

3. An ambiphilic cream base according to claim 1, wherein glycerol is present at 5 to 15 percent by weight of the ambiphilic cream base.

4. An ambiphilic cream base according to claim 1, wherein glycerol is present at about 10 percent by weight of the ambiphilic cream base.

5. An ambiphilic cream base according to claim 1 wherein the water-in-oil emulsifier is at least one higher aliphatic alcohol or a mixture thereof with a partial ester of glycerol with a higher aliphatic alcohol.

6. An ambiphilic cream base according to claim 5, wherein the partial ester is glycerol monostearate.

7. An ambiphilic cream base according to claim 6, wherein the water-in-oil emulsifier is present at 5 to 16 percent by weight of the ambiphilic cream base.

8. An ambiphilic cream base according to claim 6, wherein the water-in-oil emulsifier is present at 8 to 12 percent by weight of the ambiphilic cream base.

9. An ambiphilic cream base according to claim 6, wherein the water-in-oil emulsifier is present at about 10 percent by weight of the ambiphilic cream base.

10. An ambiphilic cream base according to claim 1, further comprising stabilizers, spreading agents, emollients, humectants, crystallization inhibitors, hydrocolloids, or mixtures thereof.

11. An ambiphilic cream base according to claim 1 wherein the water content is 25 to 55 weight percent, the content of glycerol, sorbitol, or mixtures thereof is 1 to 20 weight percent, and the content of isopropyl myristate is 20 to 50 weight percent relative to the total weight of the ambiphilic cream base.

12. An ambiphilic cream base according to claim 1, further comprising an effective amount of a compatible water-soluble or fat-soluble active pharmaceutical.

13. An ambiphilic cream base consisting essentially of:

(a) water;

(b) isopropyl myristate as a component of a fatty phase;

(c) oil-in-water and water-in-oil emulsifiers; and optionally, (d) glycerol, sorbitol, or mixtures thereof;

wherein each component is present in an amount effective to provide an ambiphilic cream, and provided that the ambiphilic cream contains no propylene glycol.

14. An ambiphilic cream base according to claim 1, wherein the lipids or lipid-like substances forming the fatty phase are liquid paraffin, vaseline, octyldodecanol, medium-chain-length triglycerides or mixtures thereof.

15. An ambiphilic cream base according to claim 13 wherein liquid paraffin, vaseline, octyldodecanol, medium-chain-length triglycerides or mixtures thereof are included as components of the fatty phases.

16. An ambiphilic cream base according to claim 13 wherein the water-in-oil emulsifier is at least one higher aliphatic alcohol or a mixture thereof with a partial ester of glycerol with a higher aliphatic alcohol.

17. An ambiphilic cream base according to claim 16, wherein the partial ester is glycerol monostearate.

* * * * *